United States Patent
Husson et al.

(10) Patent No.: US 10,227,368 B2
(45) Date of Patent: Mar. 12, 2019

(54) GENERATION OF GLUCOSAMINE FROM PLANT MATERIAL

(71) Applicant: NESTEC S.A., Vevey (CH)

(72) Inventors: Jwanro Husson, Notre Dame d'Oe (FR); Didier Courtois, St-Avertin (FR)

(73) Assignee: Nestec S.A., Vevey (CH)

(*) Notice: Subject to any disclaimer, the term of this patent is extended or adjusted under 35 U.S.C. 154(b) by 0 days.

(21) Appl. No.: 15/033,736

(22) PCT Filed: Nov. 5, 2014

(86) PCT No.: PCT/EP2014/073784
§ 371 (c)(1),
(2) Date: May 2, 2016

(87) PCT Pub. No.: WO2015/067640
PCT Pub. Date: May 14, 2015

(65) Prior Publication Data
US 2016/0257705 A1    Sep. 8, 2016

(30) Foreign Application Priority Data
Nov. 5, 2013   (EP) .................................. 13191665

(51) Int. Cl.
*C07H 5/06* (2006.01)
*C07H 1/08* (2006.01)
*A61K 8/60* (2006.01)
*A61Q 19/08* (2006.01)
*A61K 8/97* (2017.01)
*A23L 33/105* (2016.01)
*A61K 31/7008* (2006.01)

(52) U.S. Cl.
CPC .............. *C07H 5/06* (2013.01); *A23L 33/105* (2016.08); *A61K 8/60* (2013.01); *A61K 8/97* (2013.01); *A61K 31/7008* (2013.01); *A61Q 19/08* (2013.01); *C07H 1/08* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 2,884,411 A * | 4/1959 | Heyns | ...................... | C07H 5/06 536/55.2 |
| 3,966,891 A * | 6/1976 | Renault | ................... | C01B 17/05 423/574.1 |
| 4,225,486 A * | 9/1980 | Suzuki | ................. | C07K 14/415 530/370 |
| 5,866,142 A | 2/1999 | Riordan | | |
| 5,998,173 A | 12/1999 | Haynes et al. | | |
| 6,372,457 B1 | 4/2002 | Berry et al. | | |
| 6,413,525 B1 | 7/2002 | Mammone et al. | | |
| 6,486,307 B1 | 11/2002 | Gandhi et al. | | |
| 7,789,159 B1 * | 9/2010 | Bader | .................... | B01D 61/04 166/279 |
| 2002/0119107 A1 | 8/2002 | Varani et al. | | |
| 2003/0181419 A1 * | 9/2003 | Hwang | .............. | A61K 31/7008 514/62 |
| 2005/0239173 A1 * | 10/2005 | McFarlan | ................ | C12N 1/18 435/85 |
| 2006/0178344 A1 | 8/2006 | Anderson et al. | | |
| 2007/0088157 A1 * | 4/2007 | Hubbs | ...................... | C07H 5/06 536/55.3 |
| 2007/0141018 A1 * | 6/2007 | Courtois | .................. | A23G 3/36 424/74 |
| 2008/0200666 A1 * | 8/2008 | Courtois | ............ | A61K 31/7008 536/55.2 |

FOREIGN PATENT DOCUMENTS

| | | |
|---|---|---|
| EP | 1172041 A2 | 1/2002 |
| GB | 649791 A | 1/1951 |
| JP | S5913708 A | 1/1984 |
| WO | 0074696 A1 | 12/2000 |
| WO | 02066667 A1 | 8/2002 |
| WO | 2005053710 | 6/2005 |
| WO | 2006120007 | 11/2006 |
| WO | 2006120009 | 11/2006 |

OTHER PUBLICATIONS

Towheed, T. E. (2003). Current status of glucosamine therapy in osteoarthritis. Arthritis Care & Research: Official Journal of the American College of Rheumatology, 49(4), 601-604. (Year: 2003).*

* cited by examiner

*Primary Examiner* — Shaojia A Jiang
*Assistant Examiner* — Dale R Miller
(74) *Attorney, Agent, or Firm* — K&L Gates LLP

(57) ABSTRACT

The invention relates to an efficient and reproducible process for generating glucosamine from plants which allows high glucosamine content to be obtained while reducing the content of residual ammonium or sulfate ions. The invention also concerns food compositions or cosmetic compositions which comprise the obtained glucosamine-enriched plant compositions.

8 Claims, No Drawings

GENERATION OF GLUCOSAMINE FROM PLANT MATERIAL

CROSS REFERENCE TO RELATED APPLICATIONS

The present application is a National Stage of International Application No. PCT/EP2014/073784, filed on Nov. 5, 2014, which claims priority to European Patent Application No. 13191665.2, filed Nov. 5, 2013, the entire contents of which are being incorporated herein by reference.

TECHNICAL FIELD

The invention provides a reproducible process for generating glucosamine from plants which allows high glucosamine content to be obtained while reducing the content of residual ammonium or sulfate ions.

The invention also relates to food compositions or cosmetic compositions which comprise the obtained glucosamine-enriched plant compositions.

BACKGROUND OF THE INVENTION

The use of pure glucosamine in the treatment of joint diseases is widely described in the patent literature as well as in the scientific literature, usually in combination with other compounds or extracts from various natural sources. Pure glucosamine is added as glucosamine hydrochloride or glucosamine sulfate, and comes from shellfish hydrolysis. For example, WO2000/0074696 describes "Herbal compositions comprising glucosamine and *Trypterygium wilfordii*, *Ligustrum lucidum* and/or *Erycibe schmidtii*, for treating inflammation or degeneration of joint tissues, e.g. arthritis" where pure glucosamine is mixed with plant preparation. Other patents relate to compositions of plant carbohydrates as dietary supplements where glucosamine is originated from chitin, i.e. once again from shellfish hydrolysis (see for example EP 1172041 or EP 0923382).

The use of glucosamine as an anti-osteoarthritis agent has been intensively developed during the last decade. Glucosamine is suspected to be the sole active compound on joint disease such as osteoarthritis. Until recently, only symptomatic treatment such as non-steroidal anti-inflammatory drugs have been thought to be efficient.

Interestingly, glucosamine is also related to the aging process of skin, which has been characterized mainly by the continuous loss of elasticity and the loss of moisture. Skin aging is reflected by major structural changes and variations in composition. Most notably aged skins have less collagen and glycosaminoglycans compared with young skins. Glycosaminoglycan molecules produced by the skin include hyaluronic acid (poly D-glucuronic acid-N-acetyl-D-glucosamine), chondroitin sulfate, and dermatan sulfate. Hyaluronic acid is produced in higher quantities by the skin cells in response to exfoliation. Hyaluronic acid has a large capacity for hydration.

Glucosamine has been shown to significantly reduce dryness of the skin and exfoliation. Glucosamine increases the moisture content and improves the smoothness of the skin. These findings suggest that long-term intake of glucosamine is effective in improving moisture content and smoothness of the skin.

It has been shown that oral supplement containing glucosamine lead to a reduction in the number of visible wrinkles and in the number of fine lines in a group of women who took the supplement. The use of an oral supplement containing glucosamine, minerals, and various antioxidant compounds can potentially improve the appearance of visible wrinkles and fine lines.

U.S. Pat. No. 6,413,525 describes methods of substantially exfoliating the skin. In particular, it relates to topically applied compositions containing an amino sugar in the form of N-acetyl-D-glucosamine. N-acetyl-D-glucosamine is known to be a rate-limiting factor in the hyaluronic acid production by living cells. The topical application of glucosamine assists in the continued production of hyaluronic acid.

Other compositions for topical application containing N-acetyl-D-glucosamine have also been disclosed, for example, in JP 59 013 708 (soften and moisturize the skin) or U.S. Pat. No. 5,866,142 (a composition for exfoliating the skin).

Glucosamine, 2-amino-2-deoxy-D-glucose, is a naturally occurring derivative of fructose and is an essential component of glycoproteins and proteoglycans, important constituents of many eukaryotic proteins. This is an essential component of mucopolysaccharides and chitin. Glycosaminoglycans (mucopolysaccharides) are large complexes incorporated into connective tissue, skin, tendons, ligaments and cartilage.

Industrial glucosamine is a pure compound obtained from the acidic hydrolysis of chitin from shellfish, a complex carbohydrate derived from N-acetyl-D-glucosamine. As an example, U.S. Pat. No. 6,486,307 describes an improved method for chitin acidic hydrolysis: a method of producing glucosamine hydrochloride from chitin by grinding the chitin to a very fine size and digesting it with concentrated hydrochloric acid.

Glucosamine can also be produced from enzymatic hydrolysis of shellfish. As an example, U.S. Pat. No. 5,998,173 describes a process for directly producing N-acetyl-D-glucosamine from chitin utilizing an ensemble of the chitinase family of enzymes to hydrolyze chitin of crustacean shells.

Patents have also been filed in relation with microbial fermentation processes where cultivated microorganisms biosynthesize glucosamine. As an example, U.S. Pat. No. 6,372,457 describes a method and material for producing glucosamine by fermentation using a genetically modified microorganism.

All these processes concern the production of pure, extracted glucosamine, in competition with shellfish extracts.

GB 649 791 concerns an improved process of drying chicory. This process comprises the steps of: cutting chicory roots, fermenting the chicory roots under anaerobic conditions at temperatures not substantially exceeding 70° C. (best temperatures between 50 and 55° C.) for 7 h to 8 h, and drying chicory at 150° C. for about 30 minutes. However, these conditions do not allow generating glucosamine.

WO2005/053710 shows that glucosamine can be formed from several raw plant materials by following a special drying process, therefore obtaining glucosamine contents of between 150 and 1000 mg per kg of dry matter.

WO2006/120009 describes a process for generating glucosamine from plants wherein fresh plant materials, or re-hydrated dried plant materials or plant extracts, are heated at a temperature comprised between 70° C. and 110° C. for more than 10 h, wherein a glucosamine precursor, such as ammonium sulfate salt, is added to said plant materials, rehydrated plant materials or plant extracts.

WO2006/120007 relates to a process for generating glucosamine from plants similar to the one described in WO2006/120009, wherein a fertilizer acting as glucosamine precursor is added during the cultivation of the plants, before the harvest.

Although the processes described in WO2006/120007 and WO2006/120009 lead to plant raw materials containing level of glucosamine higher than 0.5% based on dry matter (i.e. 5 g of glucosamine per kg of dry matter), these processes are difficult to control. For example, the content of glucosamine in the product obtained depends, in particular, on the volume of processed raw material and the volume of the drying chamber.

Moreover, the heating process requires a limited thickness (few centimeters) of the plant material to be efficient, with high variations of the heating duration depending on the thickness. Consequently, processing large volumes of material at the industrial scale will require very large surface for the drying.

Therefore, there is a strong need for a well-controlled process managing the generation of glucosamine at a given temperature.

In addition, the raw material or plant extract obtained through the processes described in WO2005/053710, WO2006/120007 and WO2006/120009 contains high amounts of glucosamine but also high amount of residual ammonium or sulfate ions (up to, respectively, 4% and 24% based on dry matter), which can be detrimental for certain uses in food or cosmetic applications.

It is therefore an object of the invention to provide a process for generating glucosamine from plant, or to at least provide a useful alternative, where said process is reproducible.

It is another object of the invention to provide a processed plant material which contains a high amount of glucosamine and a small amount of residual ammonium or sulfate ions.

SUMMARY OF THE INVENTION

In a first aspect of the invention there is provided a process for generating glucosamine from plants comprising the following successive steps:
placing a plant material and at least one glucosamine precursor, into a receptacle,
closing said receptacle,
heating said receptacle at a temperature of 70° C. to 110° C. for more than 10 h.

In another aspect of the invention there is provided a glucosamine-enriched plant composition obtainable by the process according to the invention.

Preferably, said glucosamine-enriched plant compositions contain a reduced amount of residual ammonium or sulfate ions.

In a further aspect, the invention relates to food compositions or cosmetic compositions which comprise said glucosamine-enriched plant composition obtainable by the process as described above.

DETAILED DESCRIPTION

The invention provides a reproducible process for generating glucosamine from plant which allows high glucosamine content to be obtained while reducing the content of residual ammonium or sulfate ions.

The process according to the invention is reproducible and, in particular, it does not require specific weight and/or volume for the starting plant materials.

In the present specification, glucosamine, sulfate and ammonium contents are expressed either in percentages based on dry matter or in g per kg of dry matter unless indicated otherwise.

The word "heating" (and derived "heated"), as used herein, refers to a heating process in the range of temperature between about 70° C. and 110° C., for more than 10 h and, preferably, for less than one week. This heating process can be described as a drying process. The heating process can also consist in a liquid maceration, carried out at the same temperature and time conditions, and then followed by a drying phase.

In the present specification, by "free glucosamine", it has to be understood non-polymerized glucosamine.

In the present specification, "high amount of glucosamine" or "high glucosamine content", as used therein, means that the amount of glucosamine is higher than traces of glucosamine, higher than the amounts in the corresponding fresh (i.e. non-dried) material and higher than any content cited in literature or patents. In particular, glucosamine is present in amounts higher than 0.5% based on dry matter, preferably greater than 5% and, in particular, greater than 10% based on dry matter.

As used in this specification, the "glucosamine-enriched plant composition" refers to the product obtained through the process according to the invention with or without extraction or purification steps. This glucosamine-enriched plant composition comprises a high amount of glucosamine as defined above.

The words "plant" and "plant material", as used herein, are considered as synonyms. By "plant" or "plant material", it has to be understood any plant material capable of generating glucosamine according to the process of the invention. The plant material used can be any part of the plant, e.g. leaves, tubers, fruits, seeds, roots, grains or cell cultures. Said plant material can also be any type of plant extract obtained by any extraction procedure known to the skilled person in the technical field of plant extraction, where said plant extract is capable of generating glucosamine according to the process of the invention.

As used in this specification, the words "comprises", "comprising", and similar words, are not to be interpreted in an exclusive or exhaustive sense. In other words, they are intended to mean including, but not limited to.

Any reference to prior art documents in this specification is not to be considered an admission that such prior art is widely known or forms part of the common general knowledge in the field.

In a first aspect of the invention there is provided a process for generating glucosamine from plants comprising the following successive steps:
placing a plant material and at least one glucosamine precursor, into a receptacle,
closing said receptacle,
heating said receptacle at a temperature comprised between 70° C. and 110° C. for more than 10 h.

According to the invention, the obtained glucosamine-enriched plant compositions comprise a high glucosamine content and, for example, a glucosamine content higher than 0.5% based on dry matter, preferably greater than 5% and, in particular, greater than 10% based on dry matter.

In a preferred embodiment, the plant material is a fresh plant material, or re-hydrated dried plant material.

The plant material is selected for its ability to generate free glucosamine through the process of the invention. It can comprise a mixture of plant materials which differ, for example, in the plant species used and/or in the part of plant used.

In a preferred embodiment, the plant material is the roots of the plant.

The plant material may, in particular, be selected from the group consisting of plant species containing sucrose, fructose or inulin such as *Cichorium, Daucus, Helianthus, Beta*.

In one embodiment, the plant material may be, for example, from root of chicory (*Cichorium intybus*), root of carrot (*Daucus carota*), tuber of Jerusalem artichoke (*Helianthus tuberosum*), root of beet (*Beta vulgaris*).

In a preferred embodiment, the plant species is *Cichorium intybus* used for the production of roots containing inulin, or for the production of Belgian endive in fields or in hydroponic culture systems: i.e. chicon, witloof chicory, French endive, white endive, Dutch chicory, succory, common chicory, or Italian dandelion is *Cichorium intybus*. Witloof chicory is the common name used by most horticulturists for the cultivated plant, while Belgian endive is more used for the product ultimately sold in grocery stores to consumers. Endive is the second growth of the bud from the top of a chicory root. The first growth takes place in the field on a plant grown from seed. The second growth takes place out of the field, usually in a building, in the dark. Each root has one main bud leading to the development of the chicon (endive).

In one embodiment, fresh plant material treated according to the invention or plant material treated according to the invention, can be used as starting material, and processed to obtain plant material with high glucosamine content according to the present invention.

In particular, harvested, dried and then rehydrated plant material is used as starting material.

Glucosamine may be formed in particular by the condensation of a nitrogen-containing moiety and a sugar moiety. The glucosamine precursors used according to the invention are compounds providing the nitrogen-containing moiety needed for the formation of glucosamine. Preferably, they consist in ammonium salts. Examples of such ammonium salts are ammonium nitrate, ammonium sulfate, ammonium acetate, ammonium dihydrogenophosphate or glutamine, among others. The preferred precursor of glucosamine is ammonium sulfate which has shown surprisingly good results in the process according to the invention and in WO2006/120009 and WO2006/120007.

Advantageously, according to the process of the invention, the receptacle once filled is closed. This step improves the reproducibility of the process of the invention. In particular, the content of glucosamine in the obtained glucosamine-enriched plant composition is not dependent on the volume of the processed plant material and on the volume of the drying or heating chamber. Indeed, the efficiency of the heating step according to the invention is then not dependent on the thickness of the plant material.

The receptacle, as described above, is closed with a lid just placed above it. In another embodiment according to the invention, the lid is a screw cap or for example a flip-top lid.

In particular, the receptacle as described above is a container, a jar, or a bottle.

The heating step according to the process of the invention may last from 10 h to 120 h, for example from 12 h to 96 h, in particular, from 48 h to 96 h.

The heating temperature of the process, as described above, is preferably from 70° C. to 110° C., and for example from 70° C. to 91° C. or from 75° C. to 91° C., in particular, about 75° C.

In another aspect of the invention there is provided a process for generating glucosamine from plants as described above which further comprises the following steps:
  opening said receptacle, and
  drying the obtained glucosamine-enriched plant composition.

The drying step according to the invention can be performed through any suitable known methods to the person skilled in the art wherein the temperature remains under about 110° C. in order to avoid degradation of glucosamine. For example, usual dryers can be used. It is also possible to change the pressure conditions.

In another aspect of the invention, there is provided a process for generating glucosamine from plants as described above which further comprises a step of extracting the obtained glucosamine-enriched plant compositions. This extraction step can consist, for example, in adding said obtained glucosamine-enriched plant compositions in water for about 30 min at room temperature. Alternatively, this extraction may consist in adding said obtained glucosamine-enriched plant compositions in water:ethanol (50:50) for 60 min at room temperature.

Then the resulting mixture is centrifuged and the supernatant is freeze-dried. Alternatively, said resulting mixture is filtered and the filtrate is further dried.

Preferably, said obtained glucosamine-enriched plant compositions can be extracted with a buffer solution of high pH, for example with a pH equal to or greater than 10. Carbonate buffer of pH 10.8 is preferably used for the extracting step according to the invention.

In such pH conditions, ammonium is transformed into ammonia which is volatile and thus evaporated. Accordingly, the glucosamine-enriched plant compositions so obtained comprise a reduced amount of ammonium residue and, in particular, less than 0.5% of ammonium ions and preferably less than 0.1%.

The invention further relates to a process for generating glucosamine from plants comprising a step of extracting the obtained glucosamine-enriched plant compositions with a buffer solution of pH equal to or greater than 10 as described above, which further comprises the following steps:
  adjusting the pH of the solution to 6.5 to 7,
  adding a solution of calcium chloride,
  adding ethanol.

For example, concentrated hydrochloric acid can be used in order to adjust the pH of said obtained solution to 6.5 to 7.

The addition of calcium chloride leads to the formation of calcium sulfate complex which precipitates by adding ethanol.

The glucosamine-enriched plant compositions obtained after extraction comprise reduced amounts of residual ammonium ions and sulfate ions.

High amounts of ammonium ions and/or sulfate ions in the obtained glucosamine-enriched plant materials or plant extracts may be detrimental depending on the application's field. Indeed, high amounts of ammonium and sulfate ions are known as being aggressive for the skin, eyes and mucous membranes and should thus be avoided, in particular, in cosmetic field, for example, for the preparation of topical creams.

The obtained glucosamine-enriched plant compositions which comprise reduced amounts of residual ammonium ions and sulfate ions as described above may thus be used in a wide range of applications and, for example, for the preparation of cosmetic compositions such as anti-aging topical creams.

In another aspect of the invention, there is provided a glucosamine-enriched plant composition obtainable by the process as described above. For instance, said glucosamine-enriched plant compositions comprise at least 0.5% of glucosamine based on dry matter and preferably greater than 5% of glucosamine and, in particular, greater than 10% of glucosamine based on dry matter.

In particular, said glucosamine-enriched plant compositions comprise less than 0.5% of ammonium ions based on dry matter. Preferably, it contains less than 0.5% of ammonium ions and less than 0.5% of sulfate ions based on dry matter, in particular, less than 0.1% of ammonium ions and less than 0.2% of sulfate ions based on dry matter.

In a further aspect of the invention, there are provided food compositions or cosmetic compositions which comprise the glucosamine-enriched plant compositions as described above. Preferably, said cosmetic composition is a topical cream.

The invention is further described with reference to the following examples. It will be appreciated that the invention as claimed is not intended to be limited in any way by these examples.

The skilled person will recognize many variations in these examples to cover a wide range of formulas, ingredients, processing, and mixtures to rationally adjust the naturally occurring levels of the compounds of the invention for a variety of applications.

EXAMPLE 1

Formation of Glucosamine through the Heating and Drying Process at the Lab Level 200 g of commercial dried dices of chicory roots (0.5× 0.5×0.5 cm) are soaked in a solution of ammonium sulfate 0.5 M for 3 h. After draining, dices are placed in a container with a lid just placed above. This closed container is then placed in an oven (Binder) at a temperature of 75° C. for 48 h.

Then the container is open and the dices are spread out (10 cm dice layer) for drying in the same oven, keeping the temperature at 75° C.

2 g of powdered processed chicory roots are extracted with 200 ml of water for 30 min at room temperature. After centrifugation, the supernatant is freeze-dried. An aliquot of this supernatant is used for analytical study.

Analysis of glucosamine, sulfate and ammonium:

An aliquot of the supernatant before freeze-drying is filtered on Acrodisc 0.45 μm filter.

Analysis of glucosamine is carried out on an ion exchange Dionex PA 20 capillary column (4×250 mm) with DIONEX ICS5000 apparatus.

Analysis of sulfate is carried out on an ion exchange Dionex IonPac AS11-HC12 Analytical column 4×250 mm with DIONEX ICS2500 apparatus.

Analysis of ammonium is carried out on an ion exchange Dionex Ionpac CS 12 Analytical column 4×250 mm P/N 044001 with DIONEX ICS2500 apparatus.

The results of these analyses are as follows:
Glucosamine: 10.02% based on dry matter.
Ammonium: 3.90% based on dry matter.
Sulfate 23.78% based on dry matter.

EXAMPLE 2

Formation of Glucosamine through the Heating and Drying Process at the Pilot Plant Level 10 kg of commercial dried dices of chicory roots (0.5× 0.5×0.5 cm) are soaked in a solution of ammonium sulfate 0.5M (30L) overnight. After draining, dices represent above 35 kg wet weight and are placed in two stainless steel containers (available volume 75 L each) with a lid just placed above then in an oven (Binder) at a temperature of 75° C. for 48 h.

The extraction and analytical protocols are performed as in the example 1 (with adjustment of the volume of extraction).

The results are as follows:
Glucosamine: 8.09% based on dry matter.
Ammonium: 3.2% based on dry matter.
Sulfate 22.9% based on dry matter.

EXAMPLE 3

Extraction of Glucosamine and Removal of the Ammonium Residues 2 g of powdered material processed as in the example 1 is extracted overnight by 180 ml carbonate buffer solution at pH 10.8 instead of water.

180 ml $0.1M-Na_2CO_3$ and 20 ml $0.1M-NaHCO_3$ are added; pH 10.8 at room temperature (or pH 10.6 at 37° C.). After filtration, ammonium is transformed to ammonia and evaporated using a rotary evaporator. The remaining solution is then freeze-dried.

The analytical protocol is performed as in the example 1 (with adjustment of the volume of extraction).

The results are as follows:
Glucosamine: 8.97% based on dry matter.
Ammonium: 0.07% based on dry matter.
Sulfate 21.39% based on dry matter.

This process leads to extracts containing high amount of glucosamine with only traces of ammonium residue (<0.1%).

EXAMPLE 4

Extraction of Glucosamine and Removal of the Ammonium and Sulfate Residues 2 g of powdered material processed as in the example 1 is extracted overnight by 180 ml carbonate buffer solution at pH 10.8 instead of water.

180 ml $0.1M-Na_2CO_3$ and 20 ml $0.1M-NaHCO_3$ are added; pH 10.8 at room temperature (or pH 10.6 at 37° C.). After filtration, the pH of the solution reaches 6.5-7 by adding concentrated HCl. After 15 min agitation, $CaCl_2$ is added to the solution in order to reach a concentration of 2%. After 1 h agitation, 180 ml of ethanol (EtOH) is added. A precipitation process is performed overnight at 4° C.

The solution is centrifuged and EtOH is evaporated using a rotary evaporator. The remaining solution without the EtOH is then freeze-dried.

The analytical protocol is performed as in the example 1 (with adjustment of the volume of extraction).

The results are as follows:
Glucosamine: 1.80% based on dry matter.
Ammonium: 0.07% based on dry matter.
Sulfate: 0.10% based on dry matter.

This process thus leads to extracts containing high amount of glucosamine with only traces of ammonium (<0.1%) and sulfate (<0.2%) residues.

EXAMPLE 5

Extraction of Glucosamine and Removal of the Ammonium and Sulfate Residues with $CaCl_2$ at 12% without pH Change 2 g of powdered material processed as in the example 1 is extracted by 180 ml buffer solution at pH 10.8 instead of water overnight:

180 ml 0.1M-$Na_2CO_3$ and 20 ml 0.1M-$NaHCO_3$ are added; pH 10.8 at room temperature (or pH 10.6 at 37° C.). After 15 min agitation, $CaCl_2$ is added to the solution in order to reach a concentration of 12% of $CaCl_2$ (21.6 g for 180 ml). After 1 h agitation, 180 ml of EtOH is added. A precipitation process is performed overnight at 4° C.

The solution is centrifuged and the EtOH is evaporated using a rotary evaporator. The remaining solution without the EtOH is then freeze-dried.

The analytical protocol is performed as in the example 1 (with adjustment of the volume of extraction).

The results are as follows:
Glucosamine: 0.55% based on dry matter.
Ammonium: 0.00% based on dry matter.
Sulfate: 0.04% based on dry matter.

This process leads to extracts containing high amount of glucosamine without ammonium (0%) and sulfate (traces <0.05%) residues.

Although the invention has been described by way of example, it should be appreciated that variations and modifications may be made without departing from the scope of the invention as defined in the claims. Furthermore, where known equivalents exist to specific features, such equivalents are incorporated as if specifically referred in this specification.

The invention claimed is:

1. A process for making a food or cosmetic composition, the process comprising the following successive steps:

placing a plant material and at least one glucosamine precursor into a receptacle, wherein the at least one glucosamine precursor is ammonium sulfate and the plant material is selected from the group consisting of root of *Cichorium intybus*, root of *Daucus carota*, tuber of *Helianthus tuberosum*, root of *Beta vulgaris*, and mixtures thereof; closing the receptacle;

heating the receptacle at a temperature between 70° C. and 110° C. for a time period more than 10 hours to form a glucosamine-enriched plant composition;

extracting the glucosamine-enriched plant composition with a buffer solution having a pH equal to or greater than 10 to form a glucosamine-enriched plant extract;

adjusting a pH of the glucosamine-enriched plant extract to 6.5 to 7, adding a solution of calcium chloride and adding ethanol, to form a precipitate;

separating the precipitate from the glucosamine-enriched plant extract, to form a glucosamine-enriched solution;

isolating dry matter comprising glucosamine from the glucosamine-enriched solution; and incorporating the dry matter into the food or cosmetic composition.

2. The process according to claim 1, wherein the time period of the heating is 48 hours to 96 hours.

3. The process according to claim 1, which further comprises the following steps:

opening the receptacle; and
drying the glucosamine-enriched plant composition.

4. The process according to claim 1, wherein the temperature of the heating is 75° C. to 91° C.

5. The process according to claim 1, wherein the buffer solution is a carbonate solution at pH 10.8.

6. The process according to claim 1, wherein the dry matter comprises less than 5 g of ammonium ions per kg of dry matter.

7. The process according to claim 1, wherein the dry matter comprises less than 5 g of sulfate ions per kg of dry matter.

8. The process according to claim 1, wherein the dry matter comprises less than 1 g of ammonium ions per kg of dry matter and less than 2 g of sulfate ions per kg of dry matter.

* * * * *